United States Patent
Siejko et al.

(10) Patent No.: US 7,662,104 B2
(45) Date of Patent: *Feb. 16, 2010

(54) METHOD FOR CORRECTION OF POSTURE DEPENDENCE ON HEART SOUNDS

(75) Inventors: Krzysztof Z. Siejko, Maple Grove, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 606 days.

This patent is subject to a terminal disclaimer.

(21) Appl. No.: 11/037,275

(22) Filed: Jan. 18, 2005

(65) Prior Publication Data

US 2006/0161070 A1 Jul. 20, 2006

(51) Int. Cl.
*A61B 5/02* (2006.01)
(52) U.S. Cl. ....................................... 600/528
(58) Field of Classification Search ................ 600/528, 600/513, 514, 336, 515; 607/27
See application file for complete search history.

(56) References Cited

U.S. PATENT DOCUMENTS

| 4,094,308 | A |   | 6/1978  | Cormier |
|-----------|---|---|---------|---------|
| 4,173,971 | A | * | 11/1979 | Karz ............................ 600/515 |
| 4,289,141 | A |   | 9/1981  | Cormier |
| 4,291,699 | A |   | 9/1981  | Geddes et al. |
| 4,428,380 | A |   | 1/1984  | Wong et al. |
| 4,446,872 | A |   | 5/1984  | Marsoner et al. |
| 4,548,204 | A |   | 10/1985 | Groch et al. |
| 4,628,939 | A |   | 12/1986 | Little et al. |
| 4,649,930 | A |   | 3/1987  | Groch et al. |
| 4,763,646 | A |   | 8/1988  | Lekholm |
| 4,773,401 | A |   | 9/1988  | Citak et al. |
| 4,777,960 | A |   | 10/1988 | Berger et al. |
| 4,830,006 | A |   | 5/1989  | Haluska et al. |
| 4,905,706 | A |   | 3/1990  | Duff et al. |
| 4,915,113 | A |   | 4/1990  | Holman |

(Continued)

FOREIGN PATENT DOCUMENTS

EP 297675 A1 1/1989

(Continued)

OTHER PUBLICATIONS

"International Search Report and Written Opinion for Application No. PCT/US2006/001801, date mailed Jun. 16, 2006", 12 Pages.

(Continued)

*Primary Examiner*—Carl H Layno
*Assistant Examiner*—Luther G Behringer
(74) *Attorney, Agent, or Firm*—Schwegman, Lundberg & Woessner, P.A.

(57) ABSTRACT

A system to monitor heart sounds. The system comprises an implantable heart sound sensor operable to produce an electrical signal representative of at least one heart sound, a heart sound sensor interface circuit coupled to the heart sound sensor to produce a heart sound signal, an implantable posture sensor operable to produce an electrical signal representative of a patient's posture, and a controller circuit, coupled to the heart sound sensor interface circuit and the posture circuit. The controller circuit is operable to measure at least one heart sound in correspondence with at least one sensed patient posture.

32 Claims, 5 Drawing Sheets

U.S. PATENT DOCUMENTS

| | | | |
|---|---|---|---|
| 4,967,760 A | 11/1990 | Bennett et al. | |
| 4,989,611 A | 2/1991 | Zanetti et al. | |
| 5,025,809 A | 6/1991 | Johnson et al. | |
| 5,097,831 A | 3/1992 | Lekholm | |
| 5,113,869 A | 5/1992 | Nappholz et al. | |
| 5,137,019 A | 8/1992 | Pederson et al. | |
| 5,159,932 A | 11/1992 | Zanetti et al. | |
| 5,179,947 A | 1/1993 | Meyerson et al. | |
| 5,205,283 A | 4/1993 | Olson | |
| 5,226,413 A | 7/1993 | Bennett et al. | |
| 5,292,341 A | 3/1994 | Snell | |
| 5,301,679 A | 4/1994 | Taylor | |
| 5,305,745 A | 4/1994 | Zacouto | |
| 5,321,618 A | 6/1994 | Gessman | |
| 5,337,752 A | 8/1994 | Reeves | |
| 5,391,190 A | 2/1995 | Pederson et al. | |
| 5,411,531 A | 5/1995 | Hill et al. | |
| 5,472,453 A | 12/1995 | Alt | |
| 5,496,361 A | 3/1996 | Moberg et al. | |
| 5,544,661 A | 8/1996 | Davis et al. | |
| 5,549,650 A | 8/1996 | Bornzin et al. | |
| 5,554,177 A | 9/1996 | Kieval et al. | |
| 5,593,431 A | 1/1997 | Sheldon | |
| 5,609,612 A | 3/1997 | Plicchi et al. | |
| 5,628,777 A | 5/1997 | Moberg et al. | |
| 5,674,256 A | 10/1997 | Carlson | |
| 5,685,317 A | 11/1997 | Sjostrom | |
| 5,687,738 A | 11/1997 | Shapiro et al. | |
| 5,697,375 A | 12/1997 | Hickey | |
| 5,700,283 A | 12/1997 | Salo | |
| 5,704,365 A * | 1/1998 | Albrecht et al. | 600/515 |
| 5,713,355 A * | 2/1998 | Richardson et al. | 600/336 |
| 5,725,562 A | 3/1998 | Sheldon | |
| 5,792,195 A | 8/1998 | Carlson et al. | |
| 5,836,987 A | 11/1998 | Baumann et al. | |
| 5,860,933 A | 1/1999 | Don Michael | |
| 5,935,081 A | 8/1999 | Kadhiresan | |
| 5,951,593 A | 9/1999 | Lu et al. | |
| 5,991,661 A | 11/1999 | Park et al. | |
| 6,002,777 A | 12/1999 | Grasfield et al. | |
| 6,009,349 A | 12/1999 | Mouchawar et al. | |
| 6,026,324 A | 2/2000 | Carlson | |
| 6,044,297 A | 3/2000 | Sheldon et al. | |
| 6,044,298 A | 3/2000 | Salo et al. | |
| 6,044,299 A | 3/2000 | Nilsson | |
| 6,048,319 A | 4/2000 | Hudgins et al. | |
| 6,053,872 A | 4/2000 | Mohler | |
| 6,058,329 A | 5/2000 | Salo et al. | |
| 6,064,910 A | 5/2000 | Andersson et al. | |
| 6,076,015 A | 6/2000 | Hartley et al. | |
| 6,104,949 A | 8/2000 | Pitts Crick et al. | |
| 6,115,630 A | 9/2000 | Stadler et al. | |
| 6,144,880 A | 11/2000 | Ding et al. | |
| 6,152,884 A | 11/2000 | Bjorgaas | |
| 6,161,042 A | 12/2000 | Hartley et al. | |
| 6,190,324 B1 | 2/2001 | Kieval et al. | |
| 6,193,668 B1 | 2/2001 | Chassaing et al. | |
| 6,208,900 B1 | 3/2001 | Ecker et al. | |
| 6,208,901 B1 | 3/2001 | Hartung | |
| 6,251,126 B1 | 6/2001 | Ottenhoff et al. | |
| 6,269,269 B1 | 7/2001 | Ottenhoff et al. | |
| 6,273,856 B1 | 8/2001 | Sun et al. | |
| 6,275,727 B1 | 8/2001 | Hopper et al. | |
| 6,280,409 B1 | 8/2001 | Stone et al. | |
| 6,298,269 B1 | 10/2001 | Sweeney | |
| 6,314,323 B1 | 11/2001 | Ekwall et al. | |
| 6,324,421 B1 | 11/2001 | Stadler et al. | |
| 6,351,672 B1 | 2/2002 | Park et al. | |
| 6,360,127 B1 | 3/2002 | Ding et al. | |
| 6,366,811 B1 | 4/2002 | Carlson | |
| 6,368,283 B1 | 4/2002 | Xu et al. | |
| 6,381,493 B1 | 4/2002 | Stadler et al. | |
| 6,397,100 B2 | 5/2002 | Stadler et al. | |
| 6,409,675 B1 | 6/2002 | Turcott | |
| 6,415,033 B1 | 7/2002 | Halleck et al. | |
| 6,440,082 B1 | 8/2002 | Joo et al. | |
| 6,466,821 B1 * | 10/2002 | Pianca et al. | 607/18 |
| 6,477,406 B1 * | 11/2002 | Turcott | 600/518 |
| 6,478,746 B2 | 11/2002 | Chassaing et al. | |
| 6,491,639 B1 | 12/2002 | Turcott | |
| 6,520,924 B2 | 2/2003 | Lee | |
| 6,522,923 B1 | 2/2003 | Turcott | |
| 6,527,729 B1 * | 3/2003 | Turcott | 600/528 |
| 6,531,907 B2 | 3/2003 | Dooley et al. | |
| 6,542,775 B2 | 4/2003 | Ding et al. | |
| RE38,119 E | 5/2003 | Mower | |
| 6,567,700 B1 | 5/2003 | Turcott et al. | |
| 6,575,916 B2 | 6/2003 | Halleck et al. | |
| 6,625,493 B2 | 9/2003 | Kroll et al. | |
| 6,626,842 B2 | 9/2003 | Oka | |
| 6,643,548 B1 | 11/2003 | Mai et al. | |
| 6,650,940 B1 | 11/2003 | Zhu et al. | |
| 6,658,292 B2 | 12/2003 | Kroll et al. | |
| 6,665,564 B2 | 12/2003 | Lincoln et al. | |
| 6,684,103 B2 | 1/2004 | Ding et al. | |
| 6,719,701 B2 | 4/2004 | Lade | |
| 6,752,765 B1 | 6/2004 | Jensen et al. | |
| 6,795,732 B2 | 9/2004 | Stadler et al. | |
| 6,804,558 B2 | 10/2004 | Haller et al. | |
| 6,810,284 B1 | 10/2004 | Bradley | |
| 6,810,287 B2 | 10/2004 | Zhu et al. | |
| 6,824,519 B2 | 11/2004 | Narimatsu et al. | |
| 6,827,690 B2 | 12/2004 | Bardy | |
| 6,830,548 B2 | 12/2004 | Bonnet et al. | |
| 6,845,263 B2 | 1/2005 | Kawaguchi | |
| 6,885,889 B2 | 4/2005 | Chinchoy | |
| 6,913,577 B2 | 7/2005 | Bardy | |
| 6,915,160 B2 | 7/2005 | Auricchio et al. | |
| 6,980,851 B2 | 12/2005 | Zhu et al. | |
| 7,010,342 B2 | 3/2006 | Galen et al. | |
| 7,043,305 B2 | 5/2006 | Kenknight et al. | |
| 7,065,397 B2 | 6/2006 | Galen et al. | |
| 7,072,708 B1 | 7/2006 | Andersen et al. | |
| 7,074,195 B2 | 7/2006 | Nelson et al. | |
| 7,110,804 B2 | 9/2006 | Baumer et al. | |
| 7,110,817 B2 | 9/2006 | Yu et al. | |
| 7,115,096 B2 | 10/2006 | Siejko et al. | |
| 7,123,962 B2 | 10/2006 | Siejko et al. | |
| 7,127,290 B2 | 10/2006 | Girouard et al. | |
| 7,158,830 B2 | 1/2007 | Yu et al. | |
| 7,194,306 B1 | 3/2007 | Turcott | |
| 7,209,786 B2 | 4/2007 | Brockway et al. | |
| 7,248,923 B2 | 7/2007 | Maile et al. | |
| 7,403,813 B1 * | 7/2008 | Farazi et al. | 600/515 |
| 2001/0007053 A1 | 7/2001 | Bardy | |
| 2001/0012955 A1 | 8/2001 | Goedeke et al. | |
| 2001/0047125 A1 | 11/2001 | Quy | |
| 2002/0001390 A1 | 1/2002 | Kawaguchi | |
| 2002/0016548 A1 | 2/2002 | Stadler et al. | |
| 2002/0019586 A1 | 2/2002 | Teller et al. | |
| 2002/0026103 A1 | 2/2002 | Norris et al. | |
| 2002/0026223 A1 | 2/2002 | Riff et al. | |
| 2002/0035337 A1 | 3/2002 | Oka | |
| 2002/0082645 A1 | 6/2002 | Sweeney | |
| 2002/0107450 A1 | 8/2002 | Ogura | |
| 2002/0143262 A1 | 10/2002 | Bardy | |
| 2002/0147401 A1 | 10/2002 | Oka | |
| 2002/0151812 A1 | 10/2002 | Scheiner et al. | |
| 2002/0151938 A1 | 10/2002 | Corbucci | |
| 2003/0013974 A1 | 1/2003 | Natarajan et al. | |
| 2003/0045805 A1 | 3/2003 | Sheldon et al. | |
| 2003/0055352 A1 | 3/2003 | Hayek et al. | |
| 2003/0055461 A1 | 3/2003 | Girouard et al. | |
| 2003/0069608 A1 | 4/2003 | Sweeney | |

| | | |
|---|---|---|
| 2003/0072458 A1 | 4/2003 | Halleck et al. |
| 2003/0078624 A1 | 4/2003 | Carlson et al. |
| 2003/0093002 A1 | 5/2003 | Kuo |
| 2003/0093003 A1 | 5/2003 | Watrous et al. |
| 2003/0105496 A1 | 6/2003 | Yu et al. |
| 2003/0120159 A1 | 6/2003 | Mohler |
| 2003/0158492 A1 | 8/2003 | Sheldon et al. |
| 2003/0158584 A1 | 8/2003 | Cates et al. |
| 2003/0176896 A1 | 9/2003 | Lincoln et al. |
| 2003/0208240 A1 | 11/2003 | Pastore et al. |
| 2003/0216620 A1 | 11/2003 | Jain et al. |
| 2003/0229289 A1 | 12/2003 | Mohler |
| 2003/0233132 A1 | 12/2003 | Pastore et al. |
| 2004/0024423 A1 | 2/2004 | Lincoln et al. |
| 2004/0039419 A1 | 2/2004 | Stickney et al. |
| 2004/0039420 A1 | 2/2004 | Jayne et al. |
| 2004/0064056 A1 | 4/2004 | Ogura |
| 2004/0073093 A1 | 4/2004 | Hatlestad |
| 2004/0078059 A1 | 4/2004 | Ding et al. |
| 2004/0078060 A1 | 4/2004 | Ding et al. |
| 2004/0106960 A1 | 6/2004 | Siejko et al. |
| 2004/0106961 A1 | 6/2004 | Siejko et al. |
| 2004/0106962 A1 | 6/2004 | Mai et al. |
| 2004/0111040 A1 | 6/2004 | Ni et al. |
| 2004/0122484 A1 | 6/2004 | Hatlestad et al. |
| 2004/0127792 A1* | 7/2004 | Siejko et al. ............... 600/439 |
| 2004/0138572 A1 | 7/2004 | Thiagarajan |
| 2004/0167417 A1 | 8/2004 | Schulhauser et al. |
| 2004/0176810 A1 | 9/2004 | Stadler et al. |
| 2004/0215264 A1 | 10/2004 | Van Bentem |
| 2004/0215265 A1* | 10/2004 | Keizer ......................... 607/17 |
| 2004/0225332 A1 | 11/2004 | Gebhardt et al. |
| 2004/0230243 A1* | 11/2004 | Haefner et al. ............... 607/27 |
| 2004/0236239 A1 | 11/2004 | Murray et al. |
| 2004/0254481 A1 | 12/2004 | Brodnick |
| 2004/0267147 A1 | 12/2004 | Sullivan |
| 2004/0267148 A1 | 12/2004 | Arand et al. |
| 2005/0027323 A1 | 2/2005 | Mulligan et al. |
| 2005/0033190 A1 | 2/2005 | Bauer |
| 2005/0060001 A1 | 3/2005 | Singhal et al. |
| 2005/0102001 A1 | 5/2005 | Maile et al. |
| 2005/0148896 A1 | 7/2005 | Siejko et al. |
| 2005/0148897 A1 | 7/2005 | Cho et al. |
| 2005/0149136 A1 | 7/2005 | Siejko et al. |
| 2006/0020294 A1 | 1/2006 | Brockway et al. |
| 2006/0020295 A1 | 1/2006 | Brockway et al. |
| 2006/0025699 A1 | 2/2006 | Maile et al. |
| 2006/0030892 A1 | 2/2006 | Kadhiresan et al. |
| 2006/0041280 A1 | 2/2006 | Stahmann et al. |

FOREIGN PATENT DOCUMENTS

| | | |
|---|---|---|
| EP | 0522693 | 1/1993 |
| EP | 0709058 A1 | 5/1996 |
| JP | 2000-316825 | 11/2000 |
| WO | WO-97/25098 | 7/1997 |
| WO | WO-99/10042 | 3/1999 |
| WO | WO-0156651 A1 | 8/2001 |
| WO | WO-03041797 A2 | 5/2003 |
| WO | WO-2006078757 A1 | 7/2006 |

OTHER PUBLICATIONS

Amende, I., "Hemodynamics in ischemia: diastolic phase", *Z. Kardiol.. 73 Suppl 2*, [Article in German], (1984), 127-33.

Baynham, Tamara C., et al.. "Method and Apparatus for Cardiac Protection Pacing", U.S. Appl. No. 11/129,050, filed May 13, 2005, 33 Pages.

Krayenbuhl, H. P., "Hemodynamics in ischemia. Systolic phase", *Z. Kardiol., 73 Suppl 2*, [Article in German], (1984), 119-25.

Makhoul, John, "Linear Prediction: A Tutorial Review", *Proceedings of the IEEE*, 63, (Apr. 1975), 561-580.

Panju, Akbar A., et al., "Is This Patient Having a Myocardial Infraction?", *JAMA*, 280(14), (Oct. 14, 1998), 1256-1263.

Salerno, D. M., "Seismocardiography for monitoring changes in left ventricular function during ischemia.", *Chest*, 100(4), (Oct. 1991), 991-3.

Siejko, Krzysztof Z., et al., "A Third Heart Sound Activity Index for Heart Failure Monitoring", U.S. Appl. No. 11/465,878, filed Aug. 21, 2006, 35 Pages.

Smith, Damon, et al., "Influence of the Aortic Component of the Second Heart Sound on Left Ventricular Maximal Negative dP/dt in the Dog", *Am. J. Cardiol.*, 55: 205, (1985), 205-209.

Stein, Emanuel, et al., "Rapid Interpretation of Heart Sounds and Murmurs", Baltimore : *Williams & Wilkins, 4th ed*, (1997), 85-105.

Tavel, Morton E., "The Appearance of Gallop Rhythm after Exercise Stress Testing", *Clin. Cardiol.*, vol. 19, (1996), 887-891.

Wariar, R., et al., "Systems and Methods for Multi-Axis Cardiac Vibration Measurements", U.S. Appl. No. 11/135,985, filed May 24, 2004.

Zhang, Y., et al., "Ischemia Detection Using a Heart Sound Sensor", U.S. Appl. No. 11/148,107, filed Jun. 8, 2005, 41 pgs.

"U.S. Appl. No. 10/334,694, Response filed Dec. 3, 2007 to Final Office Action mailed Oct. 1, 2007", 21 pgs.

"U.S. Appl. No. 10/334,694 Non-Final Office Action Nov. 27, 2006", 14 pgs.

"U.S. Appl. No. 10/334,694 Non-Final Office Action Apr. 20, 2007", 28 pgs.

"U.S. Appl. No. 10/334,694 Response to Non-Final Office Action filed Feb. 27, 2007", 28 pgs.

"U.S. Appl. No. 10/334,694 Response to Non-Final Office Action filed Jul. 20, 2007", 18 Pages.

"U.S. Appl. No. 10/334,694 Final Office Action mailed Oct. 1, 2007", 14 pgs.

"U.S. Appl. No. 10/703,175, Final Office Action mailed Oct. 12, 2006", 10 pgs.

"U.S. Appl. No. 10/703,175, Non-Final Office Action mailed May 10, 2006", 13 pgs.

"U.S. Appl. No. 10/703,175, Notice of Allowance mailed Mar. 19, 2007", 6 pgs.

"U.S. Appl. No. 10/703,175, Response file Dec. 12, 2006 to Final Office Action mailed Oct. 12, 2006", 21 pgs.

"U.S. Appl. No. 10/703,175, Response filed Aug. 9, 2006 to Non-Final Office Action mailed May 10, 2006", 20 pgs.

"U.S. Appl. No. 10/865,498 Non-Final Office Action mailed Sep. 11, 2006", 11 pgs.

"U.S. Appl. No. 10/865,498 Notice of Allowance mailed Dec. 6, 2006", 12 pgs.

"U.S. Appl. No. 10/865,498 Response to Non-Final Office Action filed Oct. 24, 2006", 23 pgs.

"U.S. Appl. No. 10/900,570, Non-Final Office Action mailed Jan. 10, 2008", 4 pgs.

Breithardt, O A., et al., "Acute effects of cardiac resynchronization therapy on functional mitral regurgitation in advanced systolic heart failure", *Journal of the American College of Cardiology*, 41(5), (May 21, 2003),765-70.

Carabello, B A., "Mitral valve disease", *Current Problems in Cardiology*, 18(7), (Jul. 1993),423-78.

Collins, Sean , "Diagnostic Utility of an S3 in Dyspneic ED Patients", *Inovise Medical Inc*, University of Cincinnati Medical Center, (2005),6 Pages.

Fenster, M S., et al., "Mitral regurgitation: an overview", *Curr Probl Cardiol.*, 20(4), (Apr. 1995),193-280.

Haro, Carlos , et al., "Respiration-Synchronized Heart Sound Trending", U.S. Appl. No. 11/561,428, filed Nov. 20, 2006, 54 Pages.

Kameli, Nader, "Integrated System for Managing Patients With Heart Failure", U.S. Appl. No. 11/553,103, filed Oct. 26, 2006, 41 Pages.

Palomo, A R., et al., "Echo-phonocardiographics determination of left atrial and left ventrical filling pressures with and without mitral stenosis", *Circulation*, vol. 61, No. 5, (May 1980),1043-1047.

Say, O , et al., "Classification of heart sounds by using wavelet transform", *24th Annual Conference and the Annual Fall Meeting of the Biomedical Engineering Society] EMBS/BMES Conference*, vol. 1, (2002),128-129.

Zin, Z M., et al., "Wavelet analysis and classification of Mitral regurgitation and normal heart sounds based on artificial neural networks",

*Seventh International Symposium on Signal Processing and Its Applications*, vol. 2, (Jul. 1-4, 2003),619-620.

"U.S. Appl. No. 10/334,694, Response filed Dec. 8, 2008 to Final Office Action mailed Oct. 7, 2008", 18 pgs.

"U.S. Appl. No. 10/334,694, Advisory Action mailed Dec. 23, 2008", 3 pgs.

"U.S. Appl. No. 10/334,694, Non-Final Office Action mailed Mar. 18, 2009", 15 pgs.

"U.S. Appl. No. 10/900,570, Response filed Nov. 25, 2008 to Non-Final Office Action mailed Jul. 25, 2008", 9 pages.

"U.S. Appl. No. 11/275,800, Response filed Feb. 11, 2009 mailed Dec. 11, 2008", 14 pages.

"U.S. Appl. No. 11/275,800, Final Office Action mailed on Dec. 11, 2008", 10 pgs.

"U.S. Appl. No. 10/334,694, Response filed Jun. 19, 2008 to Non-Final Office Action mailed Mar. 19, 2008", 20 pgs.

"U.S. Appl. No. 10/334,694 Non-Final Office Action mailed Mar. 19, 2008", 15 pgs.

"U.S. Appl. No. 10/900,570 Response filed Apr. 10, 2008 to Non-Final Office Action mailed Jan. 10, 2008", 7 pages.

"U.S. Appl. No. 11/148,107, Non-Final Office Action mailed Jul. 18, 2008", 8 pgs.

"U.S. Appl. No. 11/148,107, Non-Final Office Action mailed Jul. 18, 2008", 18 pages.

"U.S. Appl. No. 11/275,800, Non-Final Office Action mailed May 2, 2008", 12 pgs.

"U.S. Appl. No. 11/275,800 Response filed Aug. 29, 2008 to Non-Final Office Action mailed May 2, 2008", 13 pages.

"U.S. Appl. No. 11/277,773, Non-Final Office Action mailed Jun. 25, 2008", 16 pgs.

"U.S. Appl. No. 10/900,570, Non-Final Action mailed Jul. 25, 2008", 5 pgs.

Rosa, A., et al., "Ectopic Pacing at Physiological Rate Improves Postanoxic Recovery of the Developing Heart", *Am. J. Physiol. —Heart Circ. Physiol.*, 284, (2003), H2384-H2392.

\* cited by examiner

METHOD FOR CORRECTION OF POSTURE DEPENDENCE ON HEART SOUNDS

CROSS-REFERENCE TO RELATED APPLICATIONS

This application is related to the following co-pending, commonly assigned U.S. patent application Ser. No. 10/900,570, entitled "DETERMINING A PATIENT'S POSTURE FROM MECHANICAL VIBRATIONS OF THE HEART," filed on Jul. 28, 2004, Ser. No. 10/703,175, entitled "A DUAL USE SENSOR FOR RATE RESPONSIVE PACING AND HEART SOUND MONITORING," filed on Nov. 6, 2003, and Ser. No. 10/334,694 entitled "METHOD AND APPARATUS FOR MONITORING OF DIASTOLIC HEMODYNAMICS," filed on Dec. 30, 2002, which are hereby incorporated by reference.

TECHNICAL FIELD

The field generally relates to implantable medical devices and, in particular, but not by way of limitation, to systems and methods for monitoring the mechanical functions of the heart.

BACKGROUND

Implantable medical devices (IMDs) are devices designed to be implanted into a patient. Some examples of these devices include cardiac rhythm management (CRM) devices such as implantable pacemakers, implantable cardioverter defibrillators (ICDs), and devices that include a combination of pacing and defibrillation. The devices are typically used to treat patients using electrical therapy and to aid a physician or caregiver in patient diagnosis through internal monitoring of a patient's condition. The devices may include electrical leads in communication with sense amplifiers to monitor electrical heart activity within a patient, and often include sensors to monitor other internal patient parameters. Other examples of implantable medical devices include implantable insulin pumps or devices implanted to administer drugs to a patient.

Heart sounds are associated with mechanical activity of a patient's heart. The first heart sound (S1) is the sound made by the heart during the near simultaneous closure of the mitral and tricuspid valves. The second heart sound (S2) marks the beginning of diastole. The third heart sound (S3) and fourth heart sound (S4) are related to filling pressures of the left ventricle during diastole.

SUMMARY

This document discusses, among other things, systems and methods for monitoring heart sounds. One system embodiment includes an implantable heart sound sensor operable to produce an electrical signal representative of at least one heart sound, a heart sound sensor interface circuit coupled to the heart sound sensor to produce a heart sound signal, an implantable posture sensor operable to produce an electrical signal representative of a patient's posture, and a controller circuit. The controller circuit is coupled to the heart sound sensor interface circuit and the posture circuit and is operable to measure the at least one heart sound in correspondence with at least one sensed patient posture.

One method embodiment includes sensing at least one heart sound using an implantable medical device, determining posture information of a patient using the implantable medical device, and measuring the heart sound in correspondence with the posture information.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

Monitoring of heart sounds aids caregivers in determining the condition of a patient's heart. For example, chronic changes in S3 amplitude is correlated to left ventricular chamber stiffness and degree of restrictive filling. For a patient with congestive heart failure (CHF), S3 heart sounds become louder as the disease progresses. IMDs can include sensors to assist caregivers in monitoring internal patient parameters such as heart sounds. However, heart sound amplitude varies with patient posture. The present inventors have recognized a need for improved measurement of heart sounds.

Figure 1:
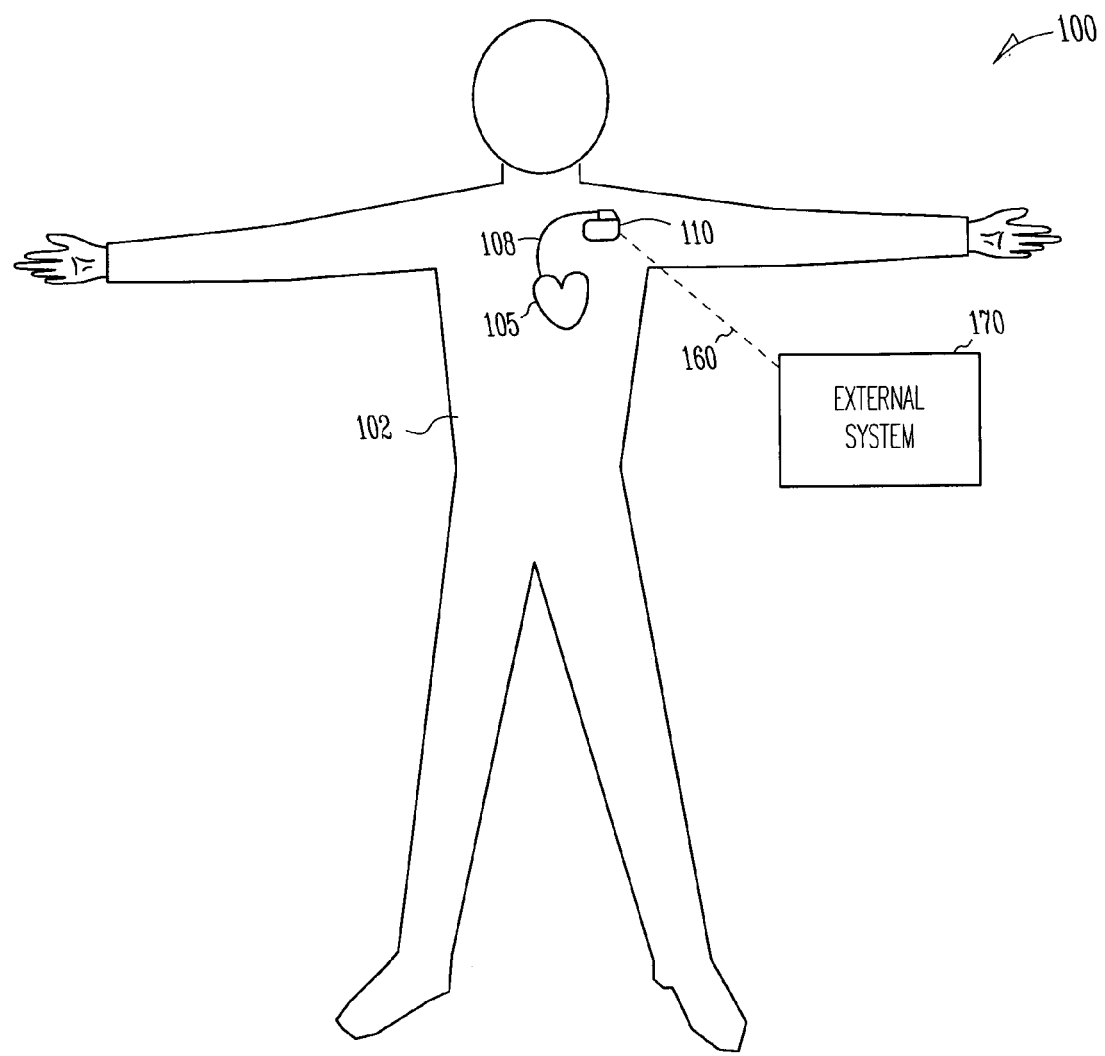
FIG. 1 illustrates an embodiment of a system that uses an implantable medical device.

The present application discusses, among other things, systems and methods for monitoring heart sounds. FIG. 1 illustrates an embodiment of a system 100 that uses an IMD 110. The system 100 shown is one embodiment of portions of a system 100 used to treat a cardiac arrhythmia or otherwise improve heart function. A pulse generator (PG) or other IMD 110 is coupled by a cardiac lead 108, or additional leads, to a heart 105 of a patient 102. Examples of IMD 110 include, without limitation, a pacer, a defibrillator, a cardiac resynchronization therapy (CRT) device, or a combination of such devices. System 100 also includes an IMD programmer or other external system 170 that provides wireless communication signals 160 to communicate with the IMD 110, such as by using radio frequency (RF) or other telemetry signals.

Cardiac lead 108 includes a proximal end that is coupled to IMD 110 and a distal end, coupled by an electrode or electrodes to one or more portions of a heart 105. The electrodes typically deliver cardioversion defibrillation, pacing, resynchronization therapy, or combinations thereof to at least one chamber of the heart 105. IMD 110 includes components that are enclosed in a hermetically-sealed canister or "can." Additional electrodes may be located on the can, or on an insulating header, or on other portions of IMD 110, for providing unipolar pacing and/or defibrillation energy in conjunction with the electrodes disposed on or around heart 105. The lead 108 or leads and electrodes are also used for sensing electrical activity of a heart 105.

Implantable heart sound sensors are generally implantable acoustic sensors that convert the detected sounds of the heart into electrical signals. An example of an acoustic sensor is an accelerometer mounted within the can. The amplitude of the several heart sounds as measured by acoustic sensors typically varies significantly with the posture of the patient when the measurement is taken. This typically confounds use of heart sound information.

Figure 2:
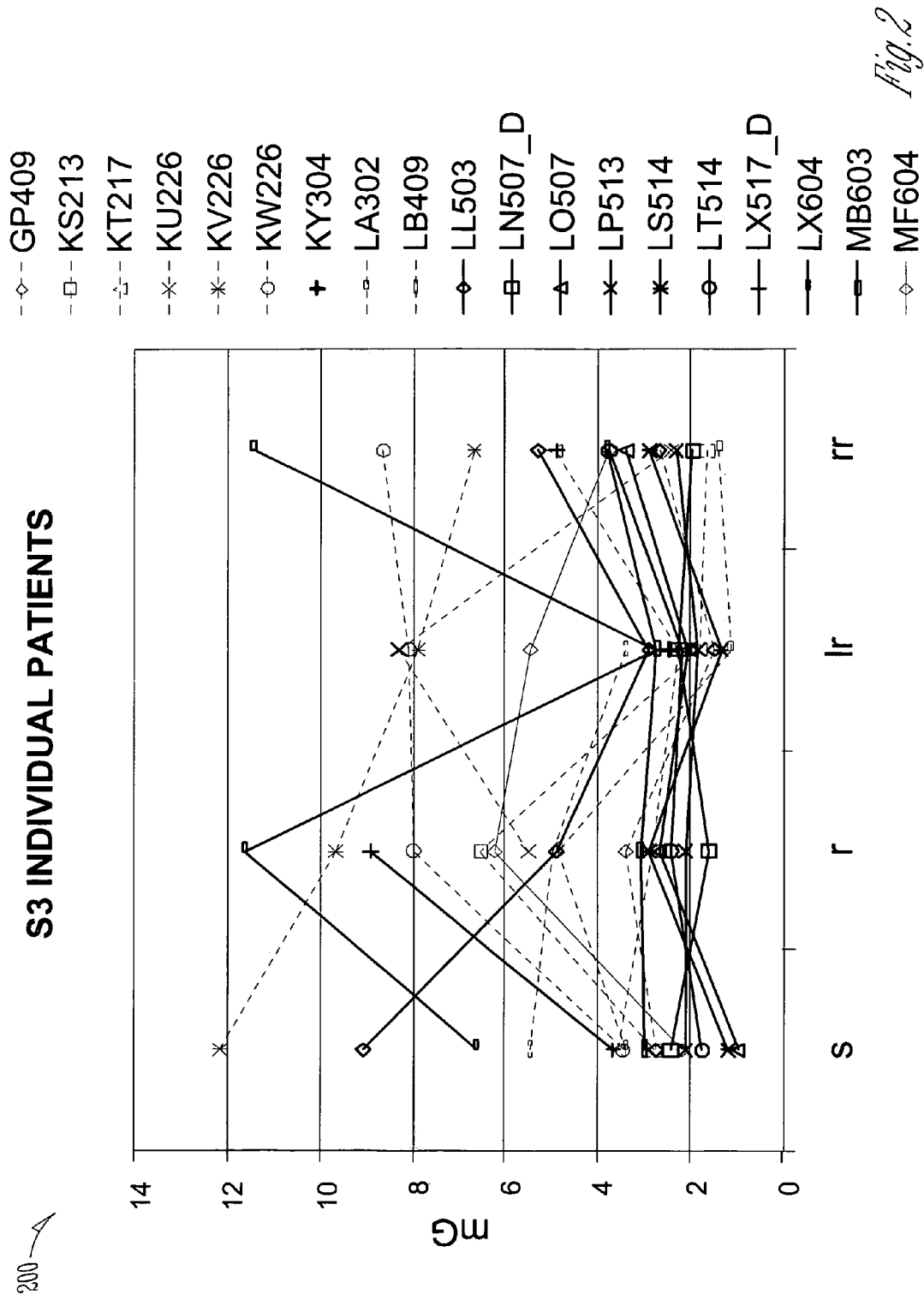
FIG. 2 is a graph of heart sound data.

FIG. 2 is a graph 200 of heart sound data taken from nineteen individuals. The data is a measure of S3 heart sounds using an accelerometer heart sound sensor while the individuals were in four postures: seated (s), recumbent (r), left recumbent (lr), and right recumbent (rr). The individuals were upright when seated, and were at an angle from 0° to 45° when recumbent. Left recumbent refers to the individual being recumbent laterally on their left side and right recumbent refers to an individual being recumbent laterally on their right side. The heart sound sensor was mounted externally on the individuals on the left side of the chest near their pectoral region. The force on the sensor was measured in milli-Gs ("G" refers to G-force, i.e. the average acceleration produced by gravity at the earth's surface). The measurements shown are peak-to-peak amplitudes.

The graph 200 shows that a change in posture for some patients can result in a change as high as 100%-200% in measured S3 amplitudes. These changes in amplitudes due to posture are caused both by changes in coupling of the heart sound sensor to the surrounding tissue and hemodynamic changes in the circulatory system. Hemodynamic changes in the circulatory system cause changes in stiffness of tissue. Because this tissue is the medium for heart sounds to propagate to the sensor, changes in the stiffness of the tissue changes the ability of the heart sound vibrations to travel through the tissue and reach the sensor. If patient posture is not accounted for in heart sound measurements, the posture dependence may mask changes in heart sounds that are actually due to disease progression, such as the increase in S3 amplitude due to CHF.

Figure 3:
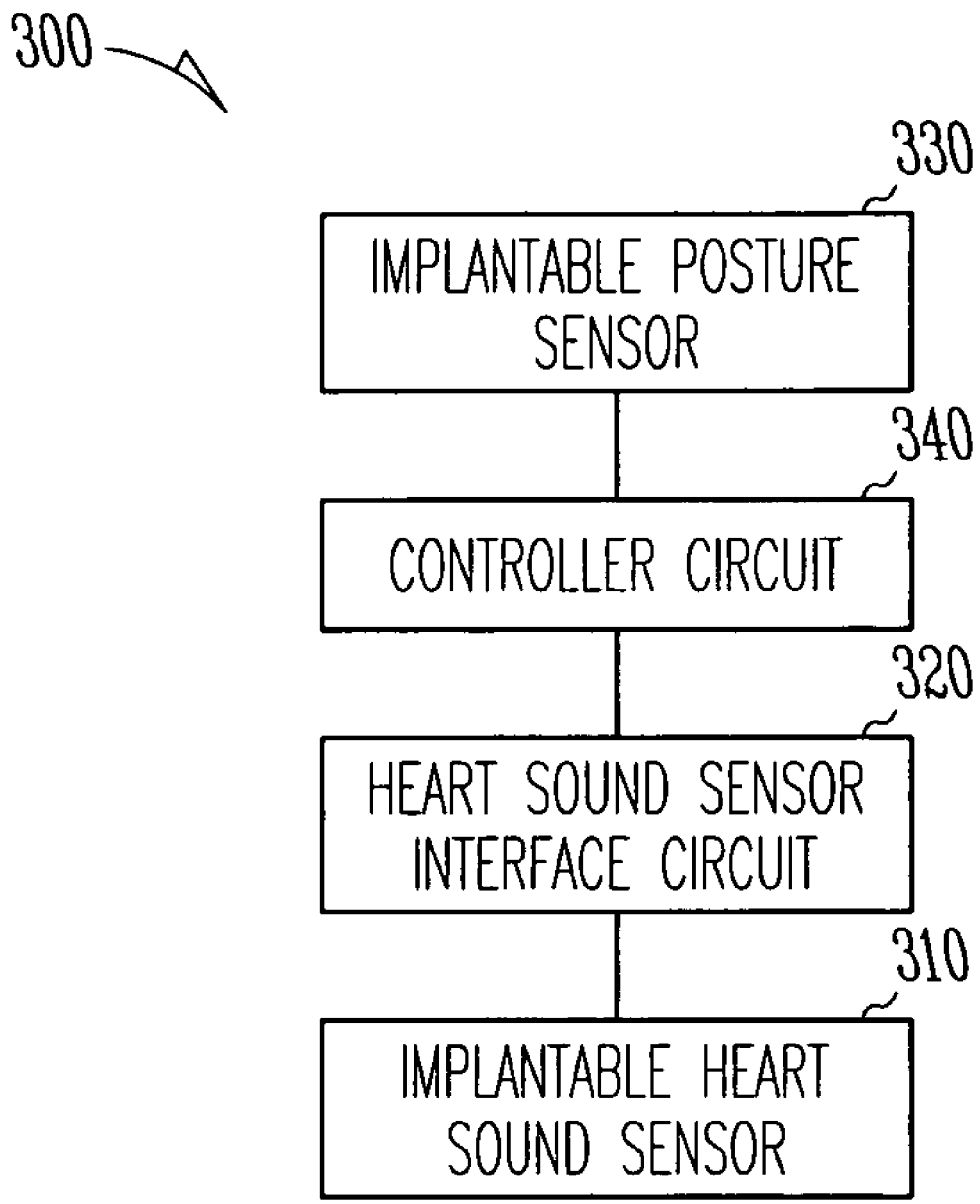
FIG. 3 shows portions of an embodiment of a system for monitoring heart sounds.

FIG. 3 shows portions of an embodiment of a system 300 for monitoring heart sounds. The system 300 includes a device that in turn includes an implantable heart sound sensor 310, a heart sound sensor interface circuit 320 coupled to the heart sound sensor 310, an implantable posture sensor 330, and a controller circuit 340 coupled to the heart sound sensor interface circuit 320 and the implantable posture sensor 330. The implantable heart sound sensor 310 is operable to produce an electrical signal representative of at least one heart sound that is associated with mechanical activity of a patient's heart. In some embodiments, the implantable heart sound sensor 310 includes an accelerometer. In some embodiments, the heart sound sensor 310 includes a strain gauge. In some embodiments, the heart sound sensor 310 includes a microphone. The heart sound sensor interface circuit 320 provides signals representative of one or more heart sounds to the controller circuit 340. Measurements of the signals are made in relation to a physiological event, such as synchronizing the measurement to a sensed heart depolarization. Descriptions of making heart sound measurements in relation to heart depolarization are found in U.S. patent application Ser. No. 10/334,694 entitled, "Method and Apparatus for Monitoring of Diastolic Hemodynamics," which is hereby incorporated by reference.

The implantable posture sensor 330 is operable to produce an electrical signal representative of a patient's posture. In some embodiments, the posture sensor 330 includes at least one DC responsive accelerometer. In some embodiments, the posture sensor 330 includes a multi-axis DC responsive accelerometer sensor. In some embodiments, the posture sensor 330 includes a mechanical tilt switch. The controller circuit 340 is operable to measure at least one heart sound in correspondence with at least one sensed patient posture using the heart sound sensor and the posture sensor. The heart sound includes at least one of the S1, S2, S3, and S4 heart sounds. In some embodiments, a heart sound measurement includes a measure of the amplitude of the heart sound signals. In some embodiments, a heart sound measurement includes sampling of the heart sound during a window of time when the heart sound occurs.

The controller circuit 340 is operable to detect a posture of the patient from a signal or signals provided by the posture sensor 330. The controller circuit 340 is operable by executing an algorithm or algorithms implemented by hardware, software, firmware or any combination of hardware, software or firmware. In some embodiments, the controller 340 executes a heart sound measurement in relation to a time of day, such as when a patient is likely to be asleep for example. In some embodiments, the measurement is made occasionally or periodically throughout the day, such as hourly. In some embodiments, the measurement is made in relation to a change in posture.

According to some embodiments, the controller is operable to measure the at least one heart sound while the patient is in an upright posture. In some embodiments, the controller 340 only executes a heart sound measurement when an upright posture is detected in the patient. An upright posture refers to a standing or a seated posture for example. In some embodiments, the device further includes a memory circuit coupled to the controller 340, and the controller 340 only stores a heart sound measurement when an upright posture is detected.

In some embodiments, the controller is operable to measure a heart sound in a plurality of postures. The heart sound measurement is made in correspondence with patient posture. In some embodiments, the heart sound measurement is stored in correspondence with a patient posture. For example, the controller 340 stores a set of heart sound measurements made when the patient is in a supine position and stores a set of heart sound measurements made when the patient is in an upright position. In another example, the controller 340 stores heart sound measurements made when the patient is in a recumbent position and when a patient is in an upright position. In some embodiments, heart sound measurements are categorized, or "binned," according to posture. Trends in the heart sounds are then determined by comparing measurements in the same "bin." Thus, problems associated with interpreting a set of heart sound measurements from varying postures are avoided.

In some embodiments, a scaling factor is applied to a heart sound measurement. The scaling factor is determined as a function of posture. The scaling factor is applied to the heart sound measurements to remove the variation with posture. For example, if S2 heart sounds for a patient in an upright position are found to have one-half the amplitude of S2 heart sounds for the patient in a recumbent position, the upright heart sound measurements are multiplied by a scaling factor of two while the recumbent heart sound measurements are multiplied by a scaling factor of one or left unaltered. If the variation with posture is removed through scaling, trends in the heart sounds can then be determined by comparing measurements directly without regard to a particular posture or bin.

According to some embodiments, the heart sounds may be stored according to seated, recumbent, and supine postures, and further, according to left and right lateral orientations. In some embodiments, the number of postures detected by the system 300 may be limited by the performance of the implantable posture sensor 330. For example, the posture sensor 330 may only be able to detect the difference between an upright posture and a supine posture. In another example, the posture sensor 330 may only be able to detect one of several postures with an accuracy of 15°. In such a case, the controller circuit 340 could be programmed to define supine as 0° to 30° as measured from the horizontal, recumbent as 30° to 60° and upright as 60° to 90°. In another example, the posture sensor 330 may be unable to detect a lateral orientation of a patient. Use of posture sensors may involve calibrating the sensors to the patient. A caregiver may put a patient in the different postures to calibrate the response of the sensor to detect that posture.

Heart sound measurements are susceptible to noise from movement and other non-cardiac vibrations such as talking. According to some embodiments, the heart sound sensor 310 is used to detect mechanical interference from non-cardiac vibrations. The controller circuit 340 uses signals provided by the heart sound sensor 310 to determine that the interference level is below a threshold interference level before a heart sound measurement is executed. In some embodiments, the controller circuit 340 determines the level of interference by monitoring the heart sound signal outside of a window of time when the heart sound occurs. In some embodiments, the controller circuit 340 determines the level of interference by a method that includes averaging the heart sound signal over a period of time. In some embodiments, the controller circuit 340 determines the level of interference by a method that includes digital signal processing (DSP) of the heart sound signal, such as to extract spectral components associated with heart sounds from interfering sounds.

Heart sound measurements are less susceptible to noise and interference from artifacts of patient movement if they are taken during a period of patient inactivity. To determine patient inactivity, some embodiments of the device further include an implantable activity sensor, such as an accelerometer (which can be the same accelerometer as the heart sound sensor or a different accelerometer). The activity sensor detects a level of patient physical activity. The controller circuit 340 is operable to measure at least one heart sound in correspondence with at least one sensed patient posture when a patient activity level is below a specified activity threshold value. For example, if the controller circuit 340 is operable to take a heart sound measurement every fifteen minutes, the controller circuit 340 may first determine if the patient is in an upright position and is inactive before executing the measurement. In some embodiments, the activity sensor is different from the heart sound sensor 310. In other embodiments, the activity sensor is the same as the heart sound sensor 310 and patient activity is determined by signal processing to isolate the activity signals.

Patient inactivity can also be determined or inferred by the time of day. Thus, in some embodiments, the device further includes a clock circuit and the controller circuit 340 is operable to measure heart sounds when it is likely that a patient is sleeping.

Patient inactivity can also be determined from other physiologic parameters. For example, a low patient heart rate may be an indication of patient inactivity. Thus, in some embodiments, the device further includes at least one implantable cardiac signal sensing circuit. The cardiac signal sensing circuit is operable to detect at least one intrinsic cardiac signal, and the controller circuit 340 is operable to measure the at least one heart sound in correspondence with at least one sensed patient posture when a patient heart rate is below a specified heart rate threshold value.

In some embodiments, patient inactivity is determined from the heart sound themselves. The controller circuit 340 detects heart sounds but waits to measure and store a heart sound until the heart sounds indicates the patient is inactive. In some embodiments, the controller makes and stores a heart sound measurement when a period of time between heart sounds are longer than a threshold period, i.e. when a heart, as determined by heart sounds, is below a threshold rate.

Patient inactivity can also be determined from a patient breathing rate. Thus, in some embodiments, the implantable medical device further includes a trans-thoracic impedance measurement circuit to provide a trans-thoracic impedance signal of a subject. The controller circuit 340 is operable to determine breathing volume from the trans-thoracic impedance signal, and to measure the at least one heart sound in correspondence with at least one sensed patient posture when a patient breathing rate is below a specified breathing rate threshold value. Illustrative examples of methods of monitoring lung tidal volume by measuring trans-thoracic impedance are described in Hartley et al. U.S. Pat. No. 6,076,015 entitled "RATE ADAPTIVE CARDIAC RHYTHM MANAGEMENT DEVICE USING TRANSTHORACIC IMPEDANCE," which is incorporated herein by reference.

According to some embodiments, one or more heart sound measurements are combined with one or more measurements of one or more other physiologic sensors, such as a trans-thoracic impedance sensor or a cardiac signal sensor, to provide a measurement of patient health. In some embodiments, one or more heart sound measurements are combined with one or more measurements of other physiologic sensors in correspondence with at least one sensed patient posture. As an example of such embodiments, trending of heart sound measurements can be combined with trans-thoracic impedance measurements in correspondence with at least one sensed patient posture to track the condition of a congestive heart failure patient. As another example, the trans-thoracic impedance measurement circuit provides a measurement of near-DC trans-thoracic impedance, and the controller is operable to provide the near-DC trans-thoracic impedance measurement in correspondence with at least one sensed patient posture and the heart sound measurement. Illustrative examples of methods of monitoring near-DC trans-thoracic impedance are described in Stahmann et al. U.S. patent application Ser. No. 10/921,503 entitled "THORACIC IMPEDANCE DETECTION WITH BLOOD RESISTIVITY COMPENSATION," which is incorporated herein by reference. Other examples of measurements of other physiologic sensors include using a measure of hematocrit in blood of the subject, or using a measure of resistivity of blood within a heart.

Figure 4:
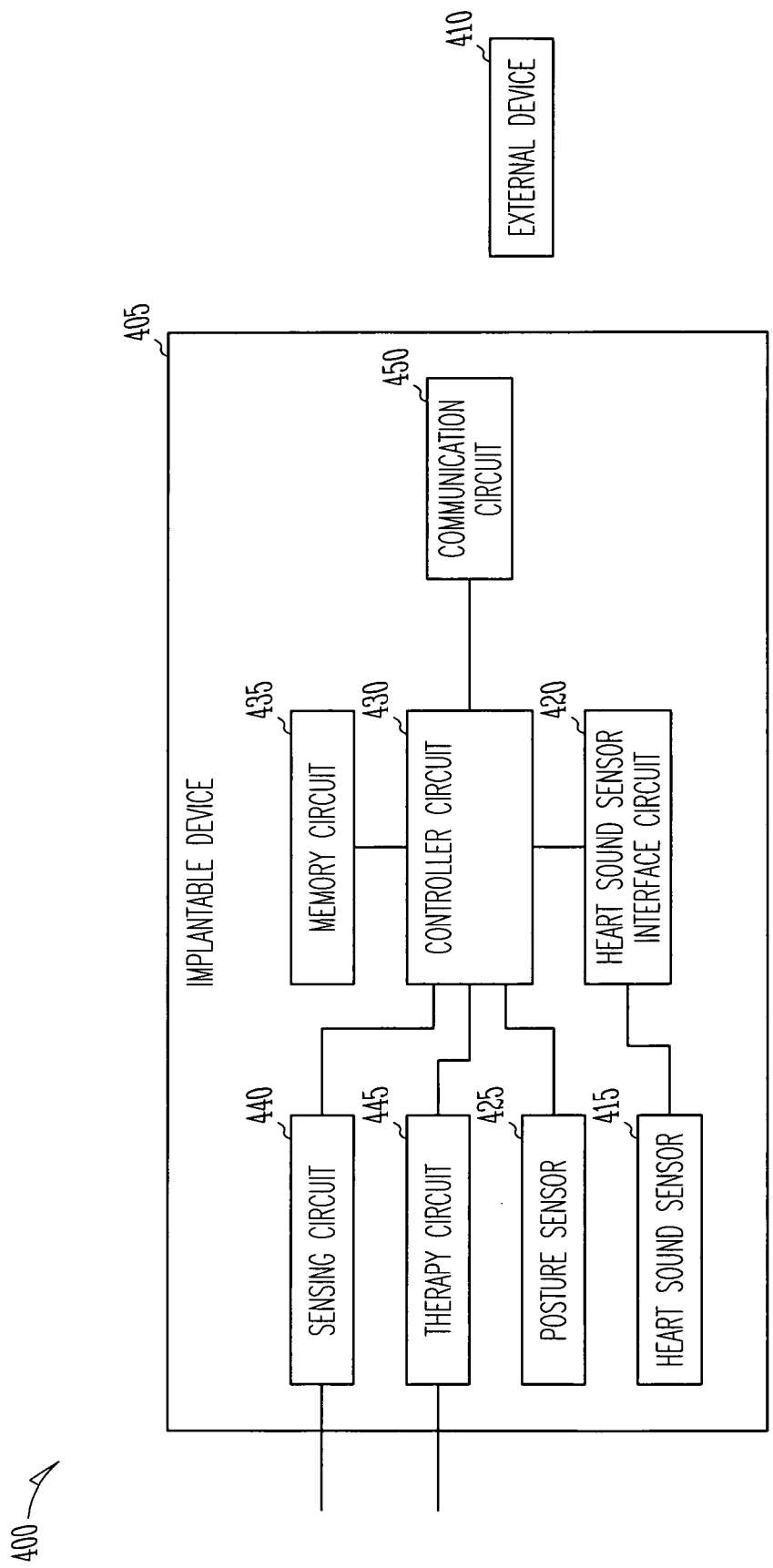
FIG. 4 shows portions of another embodiment of a system for monitoring heart sounds.

FIG. 4 shows portions of an embodiment of a system 400 for monitoring heart sounds. The system 400 includes an implantable device 405 and an external device 410 operable to communicate with the implantable device 405. The implantable device 405 includes a heart sound sensor 415, a heart sound sensor interface circuit 420, and posture sensor 425 coupled to control circuit 430. The controller circuit 430 is operable to measure the at least one heart sound in correspondence with at least one sensed patient posture. The implantable device 405 also includes a memory circuit 435, a sensing circuit 440, and a therapy circuit 445. The memory circuit 435 stores heart sound measurements. The sensing circuit 440 is coupled to a cardiac lead or leads to sense cardiac signals from a subject's heart. The therapy circuit 445 is attached to a cardiac lead or leads to provide cardioversion defibrillation, pacing, resynchronization therapy, or combinations thereof to at least one chamber of the heart.

In an embodiment, the controller circuit 430 measures the S3 heart sounds using the heart sound sensor 415 for the purpose of monitoring ventricular diastolic hemodynamic performance over time. By monitoring the posture sensor 425, the controller circuit 430 measures the S3 heart sounds while the patient is in an upright posture to reduce variations in the measurements due to patient posture. Based on the S3 heart sound measurements, the controller circuit 430 controls delivery of at least one therapy, such as pacing resynchronization therapy for example, using the therapy circuit 445.

The implantable device 405 further includes a communication circuit 450. The external device 410 communicates wirelessly with the implantable device 405 by using radio frequency (RF) or other telemetry signals. The implantable device 405 communicates heart sound information to the external device 410. In some embodiments, the external device 410 is part of, or is in communication with, a computer network such as a hospital computer network or the internet. According to some embodiments, the external device 410 is operable to communicate an alarm based on the heart sound information and the posture information. In some embodiments, the alarm includes an audio alarm or a visual alarm indication. In some embodiments, an alarm is communicated via the network to a caregiver.

According to some embodiments, the external device 410 includes a display operable to display heart sound information in relation to sensed patient posture. In some embodiments, the heart sound information includes a trend of heart sound information in relation to patient posture. The trend information is useful to establish a trend indicative of a disease status of a patient or subject. This status can be an indication of worsening status or improving status.

In some embodiments, the trend information consists entirely of heart sound information corresponding to a single posture. In some embodiments, the trend information consists of heart sound information corresponding to a range of postures, e.g., the range from a recumbent posture to an upright posture. In some embodiments, a trend is maintained for each posture. In some embodiments, heart sound variation with posture is removed by using one or more scaling factors and the heart sound information is combined into a single trend. In some embodiments, the trend or trends of heart sound information is maintained in the implantable device 405, the external device 410, or both. In some embodiments, analyses on the heart sound information for multiple separate trends, such as a separate trend for each of supine, seated, and recumbent postures are combined to form a single decision as to whether to generate an alarm. In some embodiments, the analyses are combined with one or more measurements of one or more other physiologic sensors. These analyses can be done in the implantable device 405, the external device 410, or both.

Figure 5:
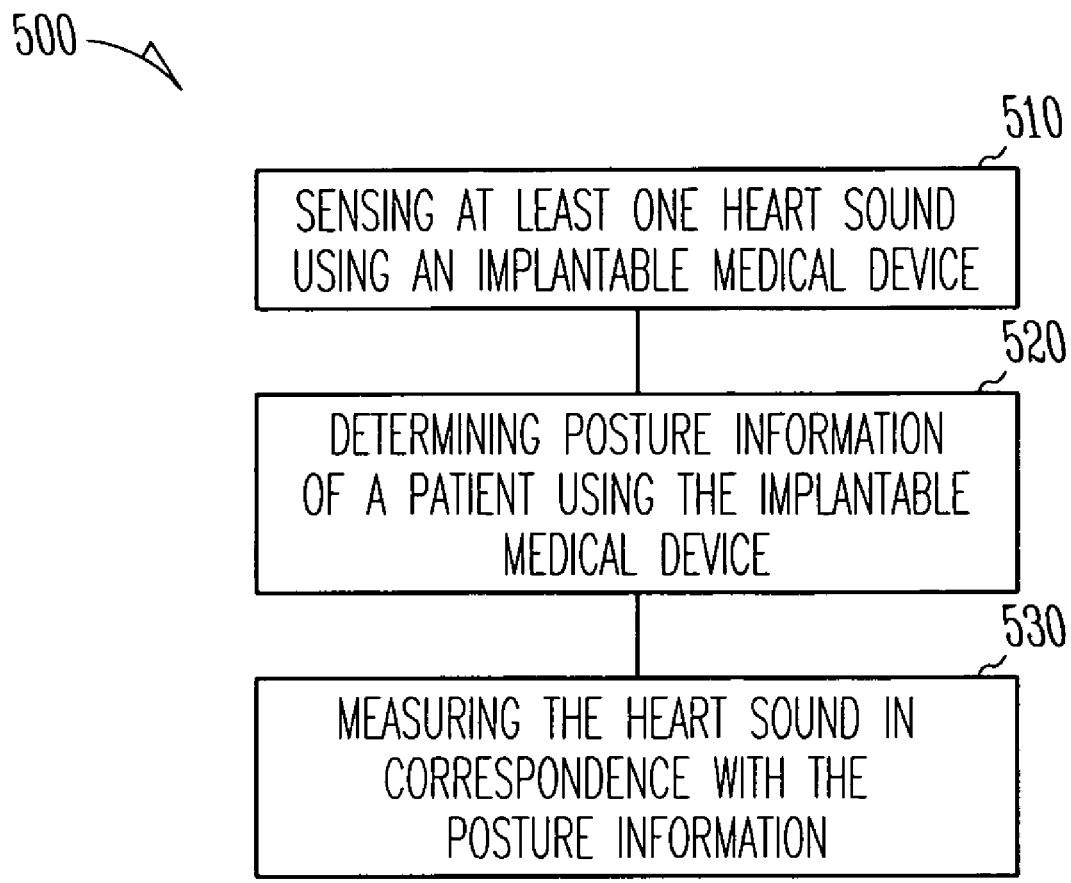
FIG. 5 is a block diagram of an embodiment of a method for monitoring heart sounds.

FIG. 5 is a block diagram of an embodiment of a method 500 for monitoring heart sounds. At 510, at least one heart sound is sensed using an implantable medical device. In some embodiments, sensing at least one heart sound includes sensing at least one of the S1, S2, S3, and S4 heart sounds, and the measurement of at least one heart sound is performed when a heart rate is below a specified heart rate threshold value. In some embodiments, the measurement of at least one heart sound is performed when a patient activity level is below a specified activity threshold value. In some embodiments, the measurement of at least one heart sound is performed when a mechanical interference level is below a threshold value.

At 520, posture information of a patient is determined using the implantable medical device, and at 530, the heart sound is measured in correspondence with the posture information. In some embodiments, measuring at least one heart sound in correspondence with the posture information includes measuring heart sounds in correspondence with respective postures and relating a heart sound measurement to a particular posture. In some embodiments, measuring the at least one heart sound in correspondence with respective postures includes applying at least one scaling factor as a function of posture to at least one heart sound measurement. In some embodiments, measuring at least one heart sound in correspondence with the patient's posture includes measuring the heart sound contingent on the patient being in a specified posture, such as for example an upright posture.

According to some embodiments, measuring at least one heart sound in correspondence with the patient's posture includes measuring at least one trend of heart sounds in relation to posture. In some embodiments the heart sound trend information is combined with trending of measurements from other physiologic sensors. In some embodiments, trending information of measurements of the at least one heart sound is stored in correspondence with the patient's posture. In some embodiments, the method 500 further includes communicating the trending information to an external device for display.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. A system comprising:
   a device comprising:
   an implantable heart sound sensor operable to produce an electrical signal representative of at least one heart sound, the heart sound associated with mechanical activity of a patient's heart;
   a heart sound sensor interface circuit coupled to the heart sound sensor to produce a heart sound signal;
   an implantable posture sensor operable to produce an electrical signal representative of a patient's posture;
   a memory circuit; and
   a controller circuit, coupled to the heart sound sensor interface circuit and the posture circuit, wherein the controller circuit is configured to:
   determine a patient posture using the posture sensor signal;
   measure the at least one heart sound in correspondence with at least one corresponding determined patient posture;
   adjust the heart sound measurement by using the corresponding determined patient posture to reduce or remove variation in the heart sound measurement due to patient posture; and
   provide the adjusted heart sound measurement to a user or an automated process.

2. The system of claim 1, wherein the controller is configured to determine the patient is in an upright posture and to measure the heart sound when the controller determines the patient is in the upright posture.

3. The system of claim 1, wherein the controller circuit is configured to:
   determine the patient is in each of a plurality of postures;
   measure the heart sound in correspondence with the determined postures; and
   reduce or remove variation in the heart sound measurement due to varying posture by relating a heart sound measurement according to a determined posture.

4. The system of claim 3, wherein the controller is configured to store at least one heart sound measurement in correspondence with or according to a determined patient posture.

5. The system of claim 3, wherein the controller is configured to reduce or remove variation in the heart sound information due to varying posture by applying a scaling factor to at least one heart sound measurement, wherein the scaling factor is a function of a patient posture.

6. The system of claim 1, wherein the device further includes a clock circuit and the controller circuit is operable to measure heart sounds at a time of day when a patient is in a recumbent posture.

7. The system of claim 1, wherein the controller circuit is operable to use the electrical signal provided by the implantable heart sound sensor to determine that mechanical interference is below a threshold level before a heart sound measurement is executed.

8. The system of claim 1, wherein the device further includes at least one implantable cardiac signal sensing circuit operable to detect at least one intrinsic cardiac signal, and wherein the controller is operable to measure the at least one heart sound in correspondence with at least one determined patient posture when a patient heart rate is below a specified heart rate threshold value.

9. The system of claim 1, wherein the device further includes an implantable activity sensor and the controller is operable to measure the at least one heart sound in correspondence with at least one sensed patient posture when a patient activity level is below a specified activity threshold value.

10. The system of claim 1, wherein the device further includes an implantable trans-thoracic impedance measurement circuit to provide a trans-thoracic impedance signal of a subject, wherein the controller is operable to provide the trans-thoracic impedance measurement in correspondence with at least one sensed patient posture and the measured heart sound.

11. The system of claim 10, wherein the trans-thoracic impedance measurement circuit provides a measurement of near-DC trans-thoracic impedance and the controller is operable to provide the near-DC trans-thoracic impedance measurement in correspondence with at least one sensed patient posture and the measured heart sound.

12. The system of claim 1, wherein the device is an implantable device and the system further includes an external device operable to communicate with the implantable device, wherein the external device includes a display, and wherein the external device is further operable to display heart sound information in relation to sensed patient posture.

13. The system of claim 12, wherein the heart sound information includes at least one trend of heart sound information in relation to patient posture.

14. The system of claim 1, wherein the device is an implantable device and the system further includes an external device operable to communicate with the implantable device, and wherein the external device is in communication with a computer network.

15. The system of claim 14, wherein the external device is operable to communicate an alarm based on trends of information that include the heart sound signal and the patient posture.

16. A method comprising:
   sensing at least one heart sound using an implantable medical device;
   determining posture of a patient using the implantable medical device;
   measuring the heart sound in correspondence with at least one corresponding determined patient posture;
   storing the heart sound measurement in conjunction with or according to the determined patient posture;
   adjusting the heart sound measurement by using the corresponding determined patient posture for reducing or removing variation in the heart sound measurement due to patient posture; and
   providing the adjusted heart sound measurement to a user or an automated process.

17. The method of claim 16, wherein reducing or removing variation in the heart sound measurement due to varying posture includes measuring heart sounds in correspondence with respective postures and relating a heart sound measurement according to a posture.

18. The method of claim 17, wherein reducing or removing variation in the heart sound measurement due to varying posture includes applying at least one scaling factor to at least one heart sound measurement, wherein the scaling factor is a function of posture.

19. The method of claim 16, wherein measuring at least one heart sound is performed when a heart rate is below a specified heart rate threshold value.

20. The method of claim 16, wherein measuring at least one heart sound in correspondence with the patient's posture-includes measuring the heart sound contingent on the implantable medical device determining the patient is in a specified posture.

21. The method of claim 20, wherein the specified posture is an upright posture.

22. The method of claim 16, wherein the measuring at least one heart sound in correspondence with the patient's posture includes measuring the at least one heart sound when a patient activity level is below a specified activity threshold value.

23. The method of claim 16, wherein the measuring at least one heart sound in correspondence with the patient's posture includes measuring the at least one heart sound when a mechanical interference level is below a threshold value.

24. The method of claim 16, wherein the measuring at least one heart sound in correspondence with the patient's posture includes measuring a trend of heart sounds in relation to posture.

25. The method of claim 16, further including storing trending information of measurements of the at least one heart sound in correspondence with the patient's posture.

26. The method of claim 25, further including communicating the trending information to an external device for display.

27. A system comprising:
an implantable medical device, the implantable medical device comprising:
a communication circuit;
a heart sound sensor operable to produce an electrical signal representative of a heart sound;
a heart sound sensor interface circuit coupled to the heart sound sensor to produce a heart sound signal;
a posture sensor operable to produce an electrical signal representative of a patient's posture; and
a controller circuit, coupled to the heart sound sensor interface circuit and the posture circuit, wherein the controller circuit is configured to:
determine a patient posture using the posture sensor signal;
measure heart sounds in correspondence with corresponding determined patient postures; and
categorize or store a heart sound measurement according to determined patient posture; and
adjust the heart sound measurement by using the corresponding determined patient posture to reduce or remove variation in the heart sound measurement due to patient posture.

28. The system of claim 27, wherein the controller circuit is configured to reduce or remove variation in the heart sound measurement due to varying posture by applying a scaling factor to the heart sound measurement, wherein the scaling factor is a function of patient posture.

29. The system of claim 28, wherein the system further includes an external device operable to communicate with the implantable device, wherein the external device includes a display, and wherein the external device is further operable to display heart sound information provided by the implantable medical device.

30. The system of claim 27, wherein the controller circuit is operable to initiate a heart sound measurement contingent on a specified patient posture.

31. The system of claim 30, wherein the specified patient posture includes an upright patient posture.

32. The system of claim 31, wherein the implantable medical device further includes an activity sensor, wherein the controller circuit is operable to initiate a heart sound measurement contingent on an upright patient posture and a patient activity being less than a specified activity threshold value.

* * * * *

UNITED STATES PATENT AND TRADEMARK OFFICE
CERTIFICATE OF CORRECTION

PATENT NO. : 7,662,104 B2
APPLICATION NO. : 11/037275
DATED : February 16, 2010
INVENTOR(S) : Siejko et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 850 days.

Signed and Sealed this

Twenty-eighth Day of December, 2010

David J. Kappos
*Director of the United States Patent and Trademark Office*